United States Patent
Bedoukian et al.

(10) Patent No.: US 9,758,475 B2
(45) Date of Patent: Sep. 12, 2017

(54) PERFUME COMPOSITIONS CONTAINING ISOMERIC ALKADIENENITRILES

(71) Applicant: BEDOUKIAN RESEARCH, INC., Danbury, CT (US)

(72) Inventors: Robert H. Bedoukian, West Redding, CT (US); Krzysztof Swierczek, Danbury, CT (US); Douglas Jay Pesak, Oxford, CT (US); Hifzur R. Ansari, Old Tappan, NJ (US)

(73) Assignee: Bedoukian Research, Inc., Danbury, CT (US)

( * ) Notice: Subject to any disclaimer, the term of this patent is extended or adjusted under 35 U.S.C. 154(b) by 89 days.

(21) Appl. No.: 14/830,313

(22) Filed: Aug. 19, 2015

(65) Prior Publication Data

US 2016/0052872 A1  Feb. 25, 2016

Related U.S. Application Data

(60) Provisional application No. 62/039,668, filed on Aug. 20, 2014.

(51) Int. Cl.
*C11B 9/00* (2006.01)
*C07C 253/30* (2006.01)
*C07C 255/07* (2006.01)

(52) U.S. Cl.
CPC .......... *C07C 253/30* (2013.01); *C07C 255/07* (2013.01); *C11B 9/0023* (2013.01); *C07B 2200/09* (2013.01)

(58) Field of Classification Search
CPC .................................................. C07C 253/30
See application file for complete search history.

(56) References Cited

U.S. PATENT DOCUMENTS 3,655,722 A  4/1972 Mitchell et al.
3,960,923 A  6/1976 DeSimone
(Continued)

OTHER PUBLICATIONS

International Search Report dated Nov. 24, 2015 from corresponding PCT Application No. PCT/US2015/045900, 3 pages.
(Continued)

*Primary Examiner* — Lanee Reuther
(74) *Attorney, Agent, or Firm* — Ohlandt, Greeley, Ruggiero & Perle, L.L.P.

(57) ABSTRACT

A perfume composition comprising an effective amount of at least one alkadienenitrile selected from 4,8-undecadienenitrile and isomers thereof, 4,9-dodecadienenitrile and isomers thereof, and 4,10-tridecadienenitrile and isomers thereof. The isomers of 4,8-undecadienenitrile comprise Z,Z-4,8-undecadienenitrile, E,E-4,8-undecadienenitrile, and mixed Z/E isomers of 4,8-undecadienenitrile; the isomers of 4,9-dodecadienenitrile comprise Z,Z-4,9-dodecadienenitrile, E,E-4,9-dodecadienenitrile, and mixed Z/E isomers of 4,9-dodecadienenitrile; and the isomers of 4,10-tridecadienenitrile comprise Z,Z-4,10-tridecadienenitrile, E,E-4,10-tridecadienenitrile, and mixed Z/E isomers of 4,10-tridecadienenitrile. A composition comprising an effective amount of at least one alkadienenitrile selected from 4,8-undecadienenitrile and isomers thereof, 4,9-dodecadienenitrile and isomers thereof, and 4,10-tridecadienenitrile and isomers thereof. Processes for the preparation of the isomeric alkadienenitriles are provided. The isomeric alkadienenitriles have a range of fresh, citric, ozonic and floral notes of exceptional strength.

14 Claims, 1 Drawing Sheet

| Material | Odor Description | Strength Scale= 0 -10 (5 panelists) |
|---|---|---|
| Z,Z-4,8-undecadienenitrile | Sweet, strong, floral | 8 |
| Isomerized 4,8-undecadienenitrile | Sweet, strong, ozonic, floral, janquille, narcissus | 8 |
| Z,Z-4,9-dodecadienenitrile | Hint of citrus, aldehydic, watery, ozonic | 6 |
| Isomerized 4,9-dodecadienenitrile | Very strong, aldehydic, watery, hint of muguet | 7 |
| Z,Z-4,10-tridecadienenitrile | Aldehydic, fatty, citrus undertones | 8 |
| Isomerized 4,10-tridecadienenitrile | Powerful, aldehydic, citrus notes of lemon/mandarin | 9 |

(56) References Cited

U.S. PATENT DOCUMENTS

| | | | |
|---|---|---|---|
| 4,235,824 A | | 11/1980 | Traas et al. |
| 5,105,005 A | * | 4/1992 | Hopp .................... C11B 9/0023 512/6 |
| 5,532,421 A | | 7/1996 | Terauchi et al. |
| 2001/0005711 A1 | * | 6/2001 | Lambrecht ............ C11B 9/0015 512/26 |
| 2006/0135400 A1 | * | 6/2006 | Kuhn ....................... A61K 8/34 512/24 |
| 2009/0148586 A1 | * | 6/2009 | Siegel ..................... A23B 7/04 426/616 |

OTHER PUBLICATIONS

Written Opinion dated Nov. 24, 2015 from corresponding PCT Application No. PCT/US2015/045900, 5 pages.

Hoernfeldt et al.; "Synthesis of C-11 Cyanoalkylphosphoranes and their Use in the Preparation of C-11-Olefins"; Acta Chemica Scandinavica, 48, Aug. 1994, vol. 48(8), pp. 665-669; DOI: 10.3891/acta.chem.scand.48-0665.

* cited by examiner

| Material | Odor Description | Strength Scale= 0 -10 (5 panelists) |
| --- | --- | --- |
| Z,Z-4,8-undecadienenitrile | Sweet, strong, floral | 8 |
| Isomerized 4,8-undecadienenitrile | Sweet, strong, ozonic, floral, janquille, narcissus | 8 |
| Z,Z-4,9-dodecadienenitrile | Hint of citrus, aldehydic, watery, ozonic | 6 |
| Isomerized 4,9-dodecadienenitrile | Very strong, aldehydic, watery, hint of muguet | 7 |
| Z,Z-4,10-tridecadienenitrile | Aldehydic, fatty, citrus undertones | 8 |
| Isomerized 4,10-tridecadienenitrile | Powerful, aldehydic, citrus notes of lemon/mandarin | 9 |

PERFUME COMPOSITIONS CONTAINING ISOMERIC ALKADIENENITRILES

RELATED APPLICATION

This application claims the benefit of copending U.S. Application No. 62/039,668, filed Aug. 20, 2014, which is incorporated herein by reference in its entirety.

BACKGROUND OF THE DISCLOSURE

1. Field of the Disclosure

This disclosure relates to isomeric alkadienenitriles and their use in perfume compositions. In particular, this disclosure relates to isomeric undecadienenitriles, dodecadienenitriles and tridecadienenitriles and their use in perfume compositions. More, in particular, this disclosure provides cis- and trans-isomers of 4,8-undecadienenitrile, 4,9-dodecadienenitrile and 4,10-tridecadienenitrile for use in perfumery applications.

2. Description of the Related Art

Aldehydes are a group of compounds with interesting odor characteristics, and have a special place in fragrance industry. They occur in nature with great abundance and are important to the characteristic odor of many fruits and flowers. However, the inherent instability of this group of materials in aggressive consumer product bases such as soaps, laundry detergents and household cleaners, etc., often becomes a major problem in their use in fragrances.

For example, citral and citronellal are natural compounds which are in part responsible for the typical and natural citrus/lemon notes and tonalities in citrus fruits and hence are highly desirable materials for the industry. Unfortunately, neither citral nor citronellal can be used as they are unstable and are chemically degraded in strong acidic or basic medium limiting their use in many important consumer products. Therefore, one long-lasting need of the industry has been to find stable substitutes for these aldehydes without compromising their fresh, natural citrus notes.

Fortunately, it was found that many nitriles mimic the overall odor of the corresponding aldehydes and could replace them in many difficult and aggressive bases. Consequently, nitriles such geranyl nitrile and citronellyl nitrile became acceptable substitutes for citral and citronellal, especially geranyl nitrile which became the most sought after nitrile to perfume household cleaning products and laundry care products for decades.

While geranyl nitrile became important to the industry, it had a significant setback on the basis of recent adverse toxicological findings and its industrial production is expected to cease in the future on these basis. Other nitriles such as citronellyl nitrile and 3,7-dimethyl-2,6-nonadiene nitrile became the replacements but with some compromise on the desirable odor notes associated with geranyl nitrile. Therefore, search for more interesting and value-added nitriles has become even more important.

Various alkenenitriles and alkadienenitriles having 10 or more carbon atoms are known as fragrance materials. For example, S. Arctander in "Perfume and Flavor Chemicals" names geranyl nitrile as a mixture of cis- and trans-isomers but without any reference to the individual cis and trans configuration. U.S. Pat. Nos. 3,655,722 and 3,960,923 describe the preparation of the mixed isomers of cis- and trans-geranyl nitrile by reacting 2-methyl-2-hepten-6-one with cyanoacetic acid and acetonitrile respectively. There is no way to know the odor differences between the two isomers when evaluated individually.

None of these publications give any indication that in particular the geometric isomers of this disclosure would be suitable ingredients for perfume formulations.

There is an ongoing interest in the fragrance industry to use new compounds that improve or enhance odor character and impart new notes to help perfumers create fragrances that excite and please the consumer.

The present disclosure provides many advantages, which shall become apparent as described below.

SUMMARY OF THE DISCLOSURE

This disclosure provides isomeric alkadienenitriles and their use in perfume compositions. In particular, this disclosure provides isomeric undecadienenitriles, dodecadienenitriles and tridecadienenitriles and their use in perfume compositions. More, in particular, this disclosure provides cis- and trans-isomers of 4,8-undecadienenitrile, 4,9-dodecadienenitrile and 4,10-tridecadienenitrile for use in perfumery applications.

This disclosure relates to the preparation of alkadienenitriles and their use in fragrance formulations. These new materials have a range of fresh, citrus, ozonic and floral notes highly desirable in creating consumer acceptable fragrances. Additionally, these materials are extremely cost effective since they possess high odor intensity and can be effective at imparting the desirable odor contribution to a fragrance at a very low concentration.

This disclosure also relates in part to a perfume composition comprising an effective amount of at least one alkadienenitrile selected from 4,8-undecadienenitrile and isomers thereof, 4,9-dodecadienenitrile and isomers thereof, and 4,10-tridecadienenitrile and isomers thereof. The isomers of 4,8-undecadienenitrile comprise Z,Z-4,8-undecadienenitrile, E,E-4,8-undecadienenitrile, and mixed Z/E isomers of 4,8-undecadienenitrile; the isomers of 4,9-dodecadienenitrile comprise Z,Z-4,9-dodecadienenitrile, E,E-4,9-dodecadienenitrile, and mixed Z/E isomers of 4,9-dodecadienenitrile; and the isomers of 4,10-tridecadienenitrile comprise Z,Z-4,10-tridecadienenitrile, E,E -4,10-tridecadienenitrile, and mixed Z/E isomers of 4,10-tridecadienenitrile.

This disclosure further relates in part to a composition comprising an alkadienenitrile selected from 4,8-undecadienenitrile and isomers thereof, 4,9-dodecadienenitrile and isomers thereof, and 4,10-tridecadienenitrile and isomers thereof. The isomers of 4,8-undecadienenitrile comprise Z,Z-4,8-undecadienenitrile, E,E-4,8-undecadienenitrile, and mixed Z/E isomers of 4,8-undecadienenitrile; the isomers of 4,9-dodecadienenitrile comprise Z,Z-4,9-dodecadienenitrile, E,E-4,9-dodecadienenitrile, and mixed Z/E isomers of 4,9-dodecadienenitrile; and the isomers of 4,10-tridecadienenitrile comprise Z,Z-4,10-tridecadienenitrile, E,E-4,10-tridecadienenitrile, and mixed Z/E isomers of 4,10-tridecadienenitrile. The composition can be a fragrance composition or a flavor composition.

This disclosure yet further relates in part to a process comprising reacting an isomeric alkenal compound with a cyanoalkyltriphenylphosphonium halide compound under reaction conditions sufficient to form an isomer mixture of an alkadienenitrile compound.

This disclosure also relates in part to a process comprising reacting an isomeric alkadienenitrile compound in the presence of an aromatic acid under reaction conditions sufficient to form an isomer mixture of the alkadienenitrile compound.

This disclosure further relates in part to an alkadienenitrile compound selected from 4,8-undecadienenitrile and isomers thereof 4,9-dodecadienenitrile and isomers thereof, and 4,10-tridecadienenitrile and isomers thereof. In an embodiment, the alkadienenitrile compound is the same alkadienenitrile in the compositions and perfume compositions of this disclosure.

The cis- and trans-isomers of 4,8-undecadienenitrile, 4,9-dodecadienenitrile and 4,10-tridecadienenitrile of this disclosure surprisingly possess extremely desirable odor character and a very low threshold of odor perception, resulting in high odor intensity when added to fragrance compositions. The high odor strength of these alkadienenitrile isomers is an attribute that allows perfumers to use trace quantities of these materials to achieve high odor impact at a low cost.

Further objects, features and advantages of the present disclosure will be understood by reference to the following drawings and detailed description.

BRIEF DESCRIPTION OF THE DRAWINGS

FIG. 1 lists odor description and strength for Z,Z-4,8-undecadienenitrile, isomerized 4,8-undecadienenitrile, Z,Z-4,9-dodecadienenitrile, isomerized 4,9-dodecadienenitrile, Z,Z-4,10-tridecadienenitrile and isomerized 4,10-tridecadienenitrile.

DESCRIPTION OF THE PREFERRED EMBODIMENTS

This disclosure provides isomeric alkadienenitriles and their use in perfume compositions. In particular, this disclosure provides isomeric undecadienenitriles, dodecadienenitriles and tridecadienenitriles and their use in perfume compositions. More, in particular, this disclosure provides cis- and trans-isomers of 4,8-undecadienenitrile, 4,9-dodecadienenitrile and 4,10-tridecadienenitrile for use in perfumery applications.

The isomeric undecadienenitriles, dodecadienenitriles and tridecadienenitriles of this disclosure have a range of fresh, citric, ozonic and floral notes of exceptional strength.

Illustrative alkadienenitriles of this disclosure are represented by the formulae set for below:

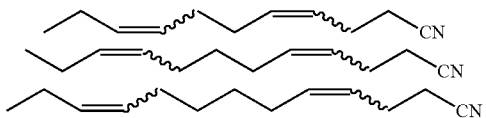

The isomeric alkadienenitriles of this disclosure have Z/E isomer ratios of their double bonds of from about 30:1 to about 1:30, or from about 12:1 to about 1:12, or from about 9:1 to about 1:9.

The isomeric alkadienenitrile composition has from about 0 percent to about 100 percent of Z,Z isomers, or from about 5 percent to about 95 percent of Z,Z isomers, or from about 20 percent to about 90 percent of Z,Z isomers, or from about 30 percent to about 85 percent of Z,Z isomers, based on the total Z and E isomers in the composition.

The isomeric alkadienenitrile composition has from about 0 percent to about 100 percent of Z,E isomers, or from about 0.5 percent to about 90 percent of Z,E isomers, or from about 1 percent to about 30 percent of Z,E isomers, or from about 2 percent to about 20 percent of Z,E isomers, based on the total Z and E isomers in the composition.

The isomeric alkadienenitrile composition has from about 0 percent to about 100 percent of E,E isomers, or from about 0.1 percent to about 50 percent of E,E isomers, or from about 1 percent to about 30 percent of E,E isomers, or from about 2 percent to about 20 percent of E,E isomers, based on the total Z and E isomers in the composition.

The isomeric alkadienenitrile composition has from about 0 percent to about 100 percent of E,Z isomers, or from about 2 percent to about 40 percent of E,Z isomers, or from about 3 percent to about 30 percent of E,Z isomers, or from about 5 percent to about 20 percent of E,Z isomers, based on the total Z and E isomers in the composition.

In accordance with this disclosure, the isomeric alkadienenitriles can be prepared by reacting an isomeric alkenal compound with a cyanoalkyltriphenylphosphonium halide compound under reaction conditions sufficient to form an isomer mixture of an alkadienenitrile compound. The alkadienenitrile compound is selected from the group consisting 4,8-undecadienenitrile and isomers thereof, 4,9-dodecadienenitrile and isomers thereof, and 4,10-tridecadienenitrile and isomers thereof. This process is exemplified in Examples 1, 4 and 7 hereinbelow and is referred to hereinafter as "Process 1".

Illustrative isomeric alkenal compounds used in the process of this disclosure include, for example, Z-4-heptenal, Z-5-octenal, Z-6-nonenal, and the like. The isomeric alkenal compounds can be used in an amount of from about 10 weight percent to about 20 weight percent, preferably from about 12 weight percent to about 18 weight percent, and more preferably from about 14 weight percent to about 16 weight percent, based on the total weight of the reaction mixture.

Illustrative cyanoalkyltriphenylphosphonium halide compounds used in the process of this disclosure include, for example, (3-cyanopropyl)triphenylphosphonium bromide, and the like. The cyanoalkyltriphenylphosphonium halide compounds can be used in an amount of from about 20 weight percent to about 35 weight percent, preferably from about 25 weight percent to about 30 weight percent, and more preferably from about 26 weight percent to about 28 weight percent, based on the total weight of the reaction mixture.

The cyanoalkyltriphenylphosphonium halide compounds can be prepared by the reaction of a cyanohaloalkyl (e.g., 4-bromobutanenitrile) compound and triphenyl phosphine to form the cyanoalkyltriphenylphosphonium halide compound. This process is exemplified in Examples 3 and 5 hereinbelow.

Other reaction ingredients can be used in amounts sufficient to prepare the isomer mixtures of the alkadienenitrile compounds in accordance with the process of this disclosure.

Illustrative isomer mixtures of the alkadienenitrile compounds prepared by the process of this disclosure include, for example, isomer mixtures of undecadienenitrile, isomer mixtures of dodecadienenitrile, isomer mixtures of tridecadienenitriles, and the like. The isomer mixtures of the alkadienenitrile compounds can be used in an amount of from about 10 weight percent to about 20 weight percent, preferably from about 12 weight percent to about 18 weight percent, and more preferably from about 14 weight percent to about 16 weight percent, based on the total weight of the reaction mixture.

With respect to Process 1, the reaction conditions for the reaction of the alkenal isomer compound with a cyanoalkyltriphenylphosphonium halide compound, such as temperature, pressure and contact time, can vary and any suitable combination of such conditions can be employed herein for preparing the isomer mixture of an alkadienenitrile compound. The reaction temperature can be between about 10° C. to about 100° C., and more preferably between about 20° C. to about 80° C., and most preferably between about 30° C. to about 50° C. Normally, the reaction is carried out under ambient pressure and the contact time can vary from a matter of seconds or minutes to a few hours or greater. The reactants can be added to the reaction mixture or combined in any order. The contact time employed can range from about 0.1 to about 24 hours, preferably from about 0.5 to 15 hours, and more preferably from about 1 to 5 hours.

Also, in accordance with this disclosure, isomeric mixtures of alkadienenitriles can be prepared by reacting an isomeric alkadienenitrile compound in the presence of an aromatic acid under reaction conditions sufficient to form an isomer mixture of an alkadienenitrile compound. This process is exemplified in Examples 2, 5 and 8 hereinbelow and is referred to hereinafter as "Process 2".

Illustrative isomeric mixtures of the alkadienenitrile compounds and reducing agents are described above.

Illustrative isomeric alkadienenitrile compounds used in the process of this disclosure include, for example, isomeric undecadienenitrile, isomeric dodecadienenitrile, isomeric tridecadienenitriles, and the like. The isomeric alkadienenitrile compounds can be used in an amount of from about 90 weight percent to about 98 weight percent, preferably from about 92 weight percent to about 96 weight percent, and more preferably from about 93 weight percent to about 95 weight percent, based on the total weight of the reaction mixture.

Illustrative isomerizing agents used in the process of this disclosure include, for example, aromatic acids such as p-toluenesulfinic acid, and the like. The isomerizing agents can be used in an amount of from about 0.5 weight percent to about 4 weight percent, preferably from about 0.75 weight percent to about 3 weight percent, and more preferably from about 0.1 weight percent to about 2 weight percent, based on the total weight of the reaction mixture.

Other reaction ingredients can be used in amounts sufficient to prepare the isomer mixtures of the alkadienenitrile compounds in accordance with the process of this disclosure.

With respect to Process 2, the reaction conditions for the reaction of the alkadienenitrile isomer compound in the presence of an isomerizing agent, such as temperature, pressure and contact time, can vary and any suitable combination of such conditions can be employed herein for preparing the isomer mixture of an alkadienenitrile compound. The reaction temperature can be between about 80° C. to about 110° C., and more preferably between about 85° C. to about 105° C., and most preferably between about 90° C. to about 100° C. Normally, the reaction is carried out under ambient pressure and the contact time can vary from a matter of seconds or minutes to a few hours or greater. The reactants can be added to the reaction mixture or combined in any order. The contact time employed can range from about 0.1 to about 24 hours, preferably from about 0.5 to 15 hours, and more preferably from about 1 to 5 hours.

In an embodiment of the present disclosure, a method of controlled production of novel cis- and trans-alkadienenitriles individually is provided. It has been found that unsaturated nitriles, especially nitriles with more than one double bond of specific geometric configuration, possess both desirable odor character and high odor intensity. For example, it has been found that various novel cis- and trans isomers of 4,8-undecadienenitrile, 4,9-dodecadienenitrile, and 4,10-tridecadienenitrile class of compounds possess highly desirable odor character and high odor intensity. The unique odor character combined with strength of these materials are the attributes that allow perfumers to achieve desirable notes and high odor impact at a low cost. See, for example, FIG. 1 which lists odor description and strength for Z,Z-4,8-undecadienenitrile, isomerized 4,8-undecadienenitrile, Z,Z-4,9-dodecadienenitrile, isomerized 4,9-dodecadienenitrile, Z,Z-4,10-tridecadienenitrile and isomerized 4,10-tridecadienenitrile. It is surprising that the odor intensity does not significantly diminish as one goes up the homologous series.

The compounds of this disclosure can be used in a broad range of fragrance applications, e.g., fine fragrances, household products, laundry products, personal care products and cosmetics. These compounds can be employed in widely varying amounts, depending upon the specific application and on the nature and amounts of other odor carrying ingredients. But because of the exceptional strength of these materials, the odor effect can be achieved at a very low level of incorporation.

Fragrances in consumer products provide several functions. They mask base odors, provide aesthetic pleasure and signal product attributes and function to the user, e.g., hygiene, cleanliness, mildness. Notwithstanding these benefits, it is also true that perfumes can cause a myriad of problems within products they have been added to, e.g. discoloration, phase separation, problems such as irritation and occasional allergic reaction to the user. Additionally, fragrances represent one of the more expensive component of the product and many fragrance ingredients may not be easily biodegradable. Over the years, perfume levels in many consumer products have increased by the popular demand but at the same time consumers have also become more critical of the fragranced products they purchase and use.

Therefore, an embodiment of this disclosure is to provide high intensity consumer acceptable fragrances desirable hedonics at a much lower concentration than achieved before. This lowering of fragrance concentration in consumer products by an order of magnitude has the benefit of cost saving, less interference with the physical properties of the product base, minimizing toxicological implications on the user, and lowering the environmental impact of chemicals used.

As used herein, the expression "perfume composition" means a mixture of fragrance materials and possibly auxiliary substances, if desired dissolved in a suitable solvent or mixed with a powdery substrate which is used to impart a desired odor to the skin and/or all types of products. Examples of such products include soaps, detergents, air fresheners, room sprays, pomanders, candles, cosmetics, such as creams, ointments, toilet waters, pre- and aftershave lotions, talcum powders, hair-care agents, body deodorants and anti-perspirants.

Fragrance materials and mixtures of fragrance materials which can be used in combination with the compounds according to this disclosure for manufacturing perfume compositions are, for example, natural products, such as essential oils, absolutes, resinoids, resins, concretes etc, but also synthetic fragrance materials such as hydrocarbons, alcohols, aldehydes, ketones, ethers, acids, esters, acetals, ketals, nitriles etc, including saturated and unsaturated compounds, aliphatic carbocyclic and heterocyclic compounds.

Examples of fragrance materials which can be used in combination with the compounds according to this disclosure include geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethyl-benzyl carbinol, trichloromethylphenyl carbinyl acetate, p-tert-butylcyclohexyl acetate, isononyl acetate, vetiveryl acetate, vetiverol, alpha-hexylcinnam-aldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentylcyclopentanone, 2-n-heptylcyclopentanone, 3-methyl-2-pentyl-2-cyclopentenone, n-decanal, n-dodecanal, 9-decen-1-01, phenoxyethylisobutyrate, phenylacetaldehydedi-methylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, aromatic nitromusks, and the like.

Auxiliary substances and solvents which can be used in perfume compositions which contain compounds according to this disclosure are, for example: ethanol, isopropanol, dipropylene glycol, dipropyleneglycol monomethyl ether, diethylphthalate, and the like.

The quantities in which the compounds according to this disclosure can be used in perfume compositions or in products to be perfumed can vary within wide limits and depend inter alia on the nature of the product in which the fragrance material is used, on the nature and quantity of the other components in the perfume composition and on the odor effect which is aimed at. It is therefore only possible to specify very rough limits, which, however, provide sufficient information for the specialist to be able to use the compounds according to the disclosure independently. In most cases a quantity of only 1 ppm in a perfume composition will already be sufficient to obtain a clearly perceptible odor effect. On the other hand, to achieve special odoriferous effects it is possible to use quantities of 100, 1000, 5000 ppm or even more in a composition. In products perfumed with such compositions, these concentrations are proportionately lower, depending on the quantity of composition used in the product.

There are three basic stages of a fragrance. The first stage (i.e., top notes) is the first impression that a fragrance gives to a customer. This initial stage is the most volatile. In the second stage (i.e., middle notes), a few moments after the application of a fragrance, the heart is revealed. This modifying part of the fragrance has medium volatility. In the third stage (i.e., base notes), after a fragrance dries down, these notes are more pronounced. This part of the fragrance is the longest lasting. The balance between these three groups is very important. In a well balanced fragrance, it is important to understand what group or groups are the most important for a particular application. The fragrance compositions of this disclosure exemplify a desirable balance between these three groups for desired applications.

The following examples are only to illustrate the preparation and use of the compounds according to the invention. The invention is not limited thereto.

EXAMPLES

Example 1

Preparation of Z,Z-4,8-Undecadienenitrile

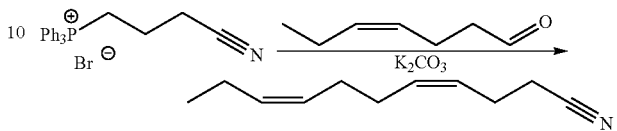

Z-4-heptenal (168.3 grams, 1.5 mol, 1.0 eq.) was fed during 4 hours to stirred mixture of (3-cyanopropyl)triphenylphosphonium bromide (615.4 grams, 1.5 mol, 1.0 eq.) and anhydrous potassium carbonate (414.6 grams, 3.0 mol, 2.0 eq.) in DMF (1000 milliliters) at 100° C. Mixture was stirred at 100° C. for additional 2.5 hours, left overnight at room temperature, diluted with water (1 L) and methanol (500 milliliters) and extracted with heptane (5×300 milliliters). Solvent was removed under reduced pressure and residue was distilled (0.5 Torr, 100-105° C.) to give product as colorless liquid (200.2 grams, yield 78.5%, purity 96.0%). Isomers: Z,Z 90.0%, E,Z 7.5%, Z,E 2.3%, E,E 0.2%.

Example 2

Preparation of Isomerized 4,8-Undecadienenitrile

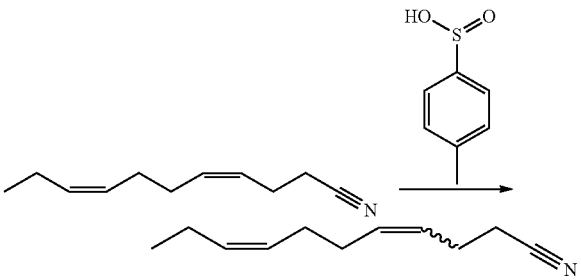

Z,Z-4,8-undecadienenitrile (96.0% pure, 10.0 grams, 0.059 mol, 1.0 eq.) was heated with p-toluenesulfinic acid (0.92 grams, 0.006 mol, 0.1 eq.) at 100° C. for 1 hour. Mixture was cooled, diluted with heptane (100 milliliters), washed with saturated aqueous sodium hydrogen carbonate (3×), water (2×) and dried with anhydrous sodium sulfate. Solvent was removed under reduced pressure. Residue was distilled (0.5 Torr, 100-105° C.) to give 4,8-undecadienenitrile (8.2 grams, yield 83.3%, purity 97.5%) as colorless liquid. Isomers: Z,Z 45.1%, E,Z 17.6%, Z,E 25.4%, E,E 11.9%.

Example 3

Preparation of Floral Fragrance Formulation

The floral fragrance formula, yellow flower, exemplified below demonstrates that the addition of Z,Z-4,8-undecadienenitrile and isomerized 4,8-undecadienal provided a clean floral fragrance with undertones of jonquille and narcissus.

| Ingredients | Parts (g) |
| --- | --- |
| Amyl Propionate | 10 |
| Alpha Pinene | 5 |
| Beta Pinene | 5 |
| Linalol | 200 |
| Geraniol | 20 |
| Nerol 10% in DPG | 10 |
| Terpineol | 20 |
| Phenyl Ethyl Alcohol | 20 |
| Benzyl Acetate | 350 |
| Methyl Benzoate | 100 |
| Methyl Salicylate | 10 |
| Benzyl Salicylate | 90 |
| Methyl-Para-Cresol 1% in DPG | 80 |
| Para-Cresyl-Acetate 1% in DPG | 20 |
| Eugenol | 20 |
| Methyl Anthranilate 10% in DPG | 10 |
| Z,Z-4,8-Undecadienenitrile 1% in DPG | 10 |
| Isomerized 4,8-Undecadienenitrile | 20 |
| Total | 1000 |

Example 4

Preparation of Z,Z-4,9-Dodecadienenitrile

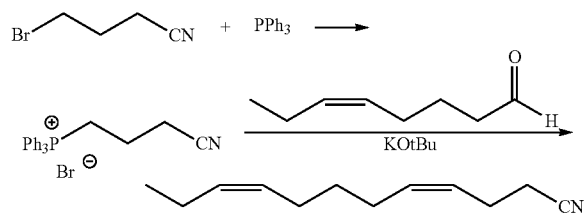

A mixture of 4-bromobutanenitrile (130.3 grams, 0.88 mol) and triphenylphosphine (239.4 grams, 0.91 mol) in diglyme (261 milliliters) was heated at 95° C. for 17.3 hours. The mixture was cooled to 90° C., then THF (379 milliliters) was added. The resulting mixture was cooled in an ice bath. Potassium tert-butoxide (105.8 grams) was then added in 10 gram portions. After 90 minutes a solution of Z-5-octenal (104.7 grams, 0.83 mol) in THF (120 milliliters) was added slowly. 45 minutes after completion of the feed the mixture was removed from the ice bath and quenched with water (345 milliliters). After stirring for 5 minutes the layers were separated. The solvents and lights were distilled from the mixture on a fractionating column ultimately taking the pot to 62° C. at 100 mmHg. After cooling, the liquid remaining in the pot was thoroughly mixed with methanol (319 milliliters), water (371 milliliters) and heptane (559 milliliters). The bottom two layers were drained together and saved. The top layer was also saved separately. The bottom two layers were diluted with methanol (157 milliliters) then extracted 3× with the following quantities of heptane (363 milliliters, 274 milliliters and 194 milliliters). All of the heptane extracts were combined then distilled on a fractionating column at reduced pressure (b.p. 77° C. at 0.2 mmHg) to give Z,Z-4,9-dodecadienenitrile (94.3 grams) as colorless liquid. Isomeric purity ~91% Z,Z.

Example 5

Preparation of Isomerized 4,9-Dodecadienenitrile

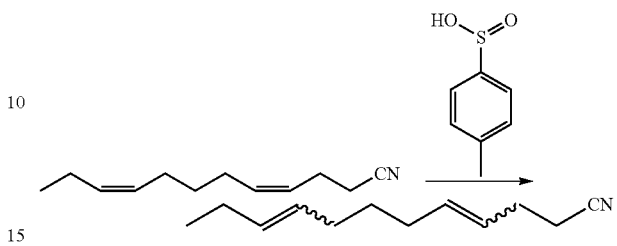

Z,Z-4,9-dodecadienenitrile (124.1 grams, 0.70 mol) was heated with p-toluenesulfinic acid (1.10 grams, 7 mmol) at 145-150° C. for 3.9 hours. Additional p-toluenesulfinic acid was added after 1.2 hours and 2.7 hours (1.08 grams and 1.10 grams, respectively). The mixture was cooled, diluted with CPME (130 milliliters) and ethanol (25 milliliters), washed with 5% NaOH (100 grams) then with 5% sodium hydrogen carbonate (100 grams). The organic layer was fractionally distilled (b.p. 82° C. at 0.3 mmHg) to give 4,9-dodecadienenitrile (90.7 grams) as colorless liquid. Isomer ratio: 4E,9E 36.1%, 4Z,9E 36.2%, 4E,9Z 13.5%, 4Z,9Z 14.2%.

Example 6

Preparation of Aldehydic Floral Fragrance Formulation

The fragrance formulation described below demonstrates that addition of relatively small quantities of Z,Z-4,9-dodecadienenitrile and isomerized 4,9-dodecadienenitrile enhances the fresh, aldehydic and floral aspects of the fragrance.

| Ingredients | Parts (g) |
| --- | --- |
| Mayol 10% in DPG | 5 |
| Undecalactone Gamma 1% in DPG | 10 |
| Hydroxycitronellal | 7 |
| Florol | 170 |
| Orange Terpenes | 4 |
| Z,Z-4,9-dodecadienenitrile 1% in DPG | 5 |
| Isomerized 4,10-tridecadienenitrile 1% in DPG | 8 |
| Dipropylene Glycol | 791 |
| Total | 1000 |

Example 7

Preparation of Z,Z-4,10-Tridecadienenitrile

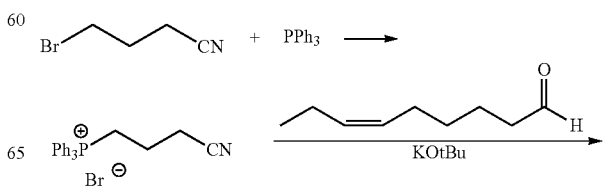

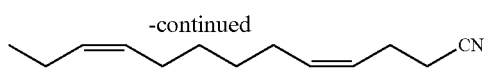

A mixture of 4-bromobutanenitrile (265.1 grams, 1.79 mol) and triphenylphosphine (492 grams, 1.88 mol) in diglyme (530 milliliters) was heated at 95° C. for 23.3 hours. The mixture was cooled to 90° C., then THF (706 milliliters) was added. The resulting mixture was cooled in an ice bath. Potassium tert-butoxide (201.3 grams) was then added in 20 gram portions. After 2 hours, a solution of Z-6-nonenal (239.3 grams, 1.71 mol) in THF (285 milliliters) was added slowly. 5 minutes after completion of the feed, the mixture was removed from the ice bath. After warming to ambient temperature overnight, the reaction was quenched with water (703 milliliters). After stirring for 10 minutes the layers were separated. The solvents and lights were distilled from the mixture on a fractionating column ultimately taking the pot to 60° C. at 100 mmHg. After cooling, the liquid remaining in the pot was thoroughly mixed with methanol (631 milliliters), water (740 milliliters) and heptane (559 milliliters). The bottom two layers were drained together and saved. The top layer was also saved separately. The bottom two layers were diluted with methanol (316 milliliters) then extracted 2× with the following quantities of heptane (721 milliliters and 544 milliliters). All of the heptane extracts were combined then distilled on a fractionating column at reduced pressure (b.p. 90° C. at 0.2 mmHg) to give Z,Z-4,10-tridecadienenitrile (241.1 grams) as colorless liquid. Isomeric purity ~92% Z,Z.

Example 8

Preparation of Isomerized 4,10-Tridecadienenitrile

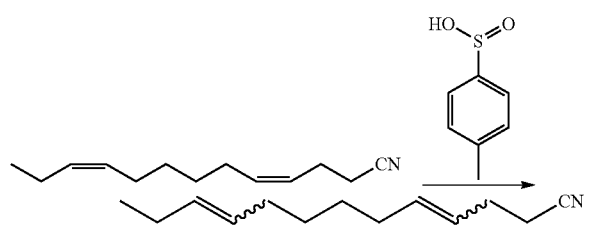

Z,Z-4,10-tridecadienenitrile (130.1 grams, 0.68 mol) was heated with p-toluenesulfinic acid (1.25 grams, 8 mmol) at 145-150° C. for 3.1 hours. Additional p-toluenesulfinic acid was added after 0.8 hours and 1.5 hours (0.33 grams and 0.32 grams, respectively). The mixture was cooled, diluted with heptane (150 milliliters) and THF (11 milliliters), washed with 5% NaOH (100 grams) then with 5% sodium hydrogen carbonate (100 grams). The organic layer was fractionally distilled (b.p. 97° C. at 0.3 mmHg) to give 4,10-tridecadienenitrile (105 grams) as colorless liquid. Isomer ratio: 4E,10E 46.3%, isomer 2 31.6%, isomer 3 12.8%, 4Z,10Z 9.2%.

Example 9

Preparation of Fresh Citrus Watery Fragrance Formulation

The fragrance formula "aquavert" described below demonstrates that the addition of isomerized 4,9-dodecadienenitrile and Z,Z-4,10-tridecadienenitrile harmonized the formulation and maximized fresh citrus top note with a watery impression.

| Ingredients | Parts (g) |
| --- | --- |
| Benzyl Acetate | 100 |
| Eucalyptol | 10 |
| 1,3,5-Undecatriene 10% in Triethyl Citrate | 20 |
| Orange Terpenes | 600 |
| Linalol | 40 |
| Linalyl Acetate | 50 |
| Galaxolide 50 | 1 |
| Hedione | 5 |
| Oxane 10% in DPG | 1 |
| Citronellal | 3 |
| Cis-3-Hexenyl Formate 10% in DPG | 30 |
| Styrallyl Acetate | 5 |
| Triplal | 20 |
| Lemon Oil | 80 |
| Citral 10% in DPG | 14 |
| Isomerized 4,9-dodecadienenitrile 1% in DPG | 10 |
| Z,Z-4,10-tridecadienenitrile 1% in DPG | 5 |
| Total | 1000 |

While we have shown and described several embodiments in accordance with our disclosure, it is to be clearly understood that the same may be susceptible to numerous changes apparent to one skilled in the art. Therefore, we do not wish to be limited to the details shown and described but intend to show all changes and modifications that come within the scope of the appended claims.

What is claimed is:

1. A composition comprising an alkadienenitrile selected from the group consisting of 4,8-undecadienenitrile and geometric isomers thereof, 4,9-dodecadienenitrile and geometric isomers thereof, and 4,10-tridecadienenitrile and geometric isomers thereof, wherein said composition is a fragrance composition or a flavor composition.

2. The composition of claim 1 wherein the isomers of 4,8-undecadienenitrile comprise Z,Z-4,8-undecadienenitrile, E,E-4,8-undecadienenitrile, and mixed Z/E isomers of 4,8-undecadienenitrile; the isomers of 4,9-dodecadienenitrile comprise Z,Z-4,9-dodecadienenitrile, E,E-4,9-dodecadienenitrile, and mixed Z/E isomers of 4,9-dodecadienenitrile; and the isomers of 4,10-tridecadienenitrile comprise Z,Z-4,10-tridecadienenitrile, E,E-4,10-tridecadienenitrile, and mixed Z/E isomers of 4,10-tridecadienenitrile.

3. The composition of claim 1 wherein the isomers of 4,8-undecadienenitrile have double bonds with a Z/E isomer ratio of from about 30:1 to about 1:30; the isomers of 4,9-dodecadienenitrile have double bonds with a Z/E isomer ratio of from about 30:1 to about 1:30; and the isomers of 4,10-tridecadienenitrile have double bonds with a Z/E isomer ratio of from about 30:1 to about 1:30.

4. The composition of claim 1 wherein the isomers of 4,8-undecadienenitrile have double bonds with a Z/E isomer ratio of from about 12:1 to about 1:12; the isomers of 4,9-dodecadienenitrile have double bonds with a Z/E isomer ratio of from about 12:1 to about 1:12; and the isomers of 4,10-tridecadienenitrile have double bonds with a Z/E isomer ratio of from about 12:1 to about 1:12.

5. The composition of claim 1 wherein the isomers of 4,8-undecadienenitrile have from about 5 percent to about 95 percent of Z,Z isomers, from about 0.5 percent to about 90 percent of Z,E isomers, from about 0.1 percent to about 50 percent of E,E isomers, and from about 2 percent to about 40 percent of E,Z isomers; the isomers of 4,9-dodecadienenitrile have from about 5 percent to about 95 percent of Z,Z isomers, from about 0.5 percent to about 90 percent of Z,E isomers, from about 0.1 percent to about 50 percent of E,E isomers, and from about 2 percent to about 40 percent of E,Z isomers; the isomers of 4,10-tridecadienenitrile have from about 5 percent to about 95 percent of Z,Z isomers, from about 0.5 percent to about 90 percent of Z,E isomers, from about 0.1 percent to about 50 percent of E,E isomers, and from about 2 percent to about 40 percent of E,Z isomers; all based on the total Z and E isomers in the composition.

6. The composition of claim 1 wherein the isomers of 4,8-undecadienenitrile are present in an amount of at least 1 ppm by weight, based on the total weight of the composition; the isomers of 4,9-dodecadienenitrile are present in an amount of at least 1 ppm by weight, based on the total weight of the composition; and the isomers of 4,10-tridecadienenitrile are present in an amount of at least 1 ppm by weight, based on the total weight of the composition.

7. A perfume composition comprising an effective amount of at least one alkadienenitrile selected from the group consisting of 4,8-undecadienenitrile and geometric isomers thereof, 4,9-dodecadienenitrile and geometric isomers thereof, and 4,10-tridecadienenitrile and geometric isomers thereof.

8. The perfume composition of claim 7 wherein the isomers of 4,8-undecadienenitrile comprise Z,Z-4,8-undecadienenitrile, E,E-4,8-undecadienenitrile, and mixed Z/E isomers of 4,8-undecadienenitrile; the isomers of 4,9-dodecadienenitrile comprise Z,Z-4,9-dodecadienenitrile, E,E-4,9-dodecadienenitrile, and mixed Z/E isomers of 4,9-dodecadienenitrile; and the isomers of 4,10-tridecadienenitrile comprise Z,Z -4,10-tridecadienenitrile, E,E-4,10-tridecadienenitrile, and mixed Z/E isomers of 4,10-tridecadienenitrile.

9. The perfume composition of claim 7 wherein the isomers of 4,8-undecadienenitrile have double bonds with a Z/E isomer ratio of from about 30:1 to about 1:30; the isomers of 4,9-dodecadienenitrile have double bonds with a Z/E isomer ratio of from about 30:1 to about 1:30; and the isomers of 4 10-tridecadienenitrile have double bonds with a Z/E isomer ratio of from about 30:1 to about 1:30.

10. The perfume composition of claim 7 wherein the isomers of 4,8-undecadienenitrile have double bonds with a Z/E isomer ratio of from about 12:1 to about 1:12; the isomers of 4,9-dodecadienenitrile have double bonds with a Z/E isomer ratio of from about 12:1 to about 1:12; and the isomers of 4,10-tridecadienenitrile have double bonds with a Z/E isomer ratio of from about 12:1 to about 1:12.

11. The perfume composition of claim 7 wherein the isomers of 4,8-undecadienenitrile have from about 5 percent to about 95 percent of Z,Z isomers, from about 0.5 percent to about 90 percent of Z,E isomers, from about 0.1 percent to about 50 percent of E,E isomers, and from about 2 percent to about 40 percent of E,Z isomers; the isomers of 4,9-dodecadienenitrile have from about 5 percent to about 95 percent of Z,Z isomers, from about 0.5 percent to about 90 percent of Z,E isomers, from about 0.1 percent to about 50 percent of E,E isomers, and from about 2 percent to about 40 percent of E,Z isomers; the isomers of 4,10-tridecadienenitrile have from about 5 percent to about 95 percent of Z,Z isomers, from about 0.5 percent to about 90 percent of Z,E isomers, from about 0.1 percent to about 50 percent of E,E isomers, and from about 2 percent to about 40 percent of E,Z isomers; all based on the total Z and E isomers in the composition.

12. The perfume composition of claim 7 wherein the isomers of 4,8-undecadienenitrile are present in an amount of at least 1 ppm by weight, based on the total weight of the composition; the isomers of 4,9-dodecadienenitrile are present in an amount of at least 1 ppm by weight, based on the total weight of the composition; and the isomers of 4,10-tridecadienenitrile are present in an amount of at least 1 ppm by weight, based on the total weight of the composition.

13. The perfume composition of claim 7 further comprising one or more of geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethyl-benzyl carbinol, trichloromethylphenyl carbinyl acetate, p-tert-butylcyclohexyl acetate, isononyl acetate, vetiveryl acetate, vetiverol, alpha-hexylcinnam- aldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(hydroxy-4-methylpentyl)-3-cyclohexenecarbaldehyde, 4-(4-methyl-3-pentenyl)-3-cyclohexenecarbaldehyde, 4-acetoxy-3-pentyl- tetrahydropyran, 3-carboxymethyl-2-pentylcyclopentanone, 2-n-heptylcyclopentanone, 3-methyl-2-pentyl-2-cyclopentenone, n-decanal, n-dodecanal, 9-decen-1-01, phenoxyethylisobutyrate, phenylacetaldehydedi-methylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, and aromatic nitromusks.

14. An alkadienenitrile compound selected from the group consisting of 4,8-undecadienenitrile and geometric isomers thereof, 4,9-dodecadienenitrile and geometric isomers thereof, and 4,10-tridecadienenitrile and geometric isomers thereof, wherein said alkadienenitrile compound is a fragrance compound or a flavor compound.

\* \* \* \* \*